United States Patent
Watabe et al.

(10) Patent No.: US 11,819,439 B1
(45) Date of Patent: Nov. 21, 2023

(54) WRIST BRACE WITH WELDED THUMB SPICA AND METHOD FOR MAKING SAME

(71) Applicant: Ovation Systems, Agoura Hills, CA (US)

(72) Inventors: Kenji Watabe, Ventura, CA (US); Tracy E. Grim, Thousand Oaks, CA (US); Zhuang Shao, Canoga Park, CA (US); Dave Cormier, Oxnard, CA (US)

( * ) Notice: Subject to any disclaimer, the term of this patent is extended or adjusted under 35 U.S.C. 154(b) by 1080 days.

(21) Appl. No.: 16/536,054

(22) Filed: Aug. 8, 2019

Related U.S. Application Data

(60) Provisional application No. 62/717,706, filed on Aug. 10, 2018.

(51) Int. Cl.
| | |
|---|---|
| *A61F 5/01* | (2006.01) |
| *B32B 5/18* | (2006.01) |
| *B29C 65/08* | (2006.01) |
| *B32B 5/02* | (2006.01) |
| *B32B 5/24* | (2006.01) |
| *B32B 27/40* | (2006.01) |
| *B32B 27/12* | (2006.01) |
| *B32B 27/06* | (2006.01) |
| *B29C 65/00* | (2006.01) |
| *B29L 31/00* | (2006.01) |

(52) U.S. Cl.
CPC ............... *A61F 5/013* (2013.01); *A61F 5/01* (2013.01); *B32B 5/02* (2013.01); *B32B 5/18* (2013.01); *B32B 5/245* (2013.01); *B32B 27/065* (2013.01); *B32B 27/12* (2013.01); *B32B 27/40* (2013.01); *A61F 2005/0186* (2013.01); *B29C 65/08* (2013.01); *B29C 66/45* (2013.01); *B29L 2031/753* (2013.01); *B32B 2305/02* (2013.01); *B32B 2535/00* (2013.01)

(58) Field of Classification Search
CPC .... A61F 5/05875; A61F 13/107; A61F 5/013; A61F 5/10; A61F 2005/0186; A61F 5/0118; A61F 5/05866; A61F 5/02; A61F 5/01; Y10S 2/91; A41D 13/088; A61H 2201/1697
See application file for complete search history.

(56) References Cited

U.S. PATENT DOCUMENTS 6,186,969 B1 * 2/2001 Bell ...................... A61F 5/0118
602/64
7,762,970 B2 * 7/2010 Henderson .......... A61F 5/05866
128/880

(Continued)

*Primary Examiner* — Ophelia A Hawthorne
(74) *Attorney, Agent, or Firm* — FULWIDER PATTON LLP

(57) ABSTRACT

A soft goods-type upper extremity orthotic is disclosed that utilizes a combination of heated 3D tooling, HF energy, and pressure to thermally bond strengthening and anchoring injection molded elements to the outer layer of a base material. The brace of the present invention may have multiple fused/welded/bonded/heat components that are strategically placed to offer support and restriction of movement of the wrist, hand, and/or thumb (WHT) for the treatment of injuries to the distal upper extremity. The components are secured to a base fabric without stitching and, in a preferred embodiment, without traditional adhesives, to provide a sturdy and robust wrist brace or upper extremity orthosis that can be manufactured far more efficiently than prior art wrist braces.

36 Claims, 13 Drawing Sheets

(56) References Cited

U.S. PATENT DOCUMENTS

| | | | |
|---|---|---|---|
| D657,094 S * | 4/2012 | Logan | D29/114 |
| D801,541 S * | 10/2017 | Wang | D24/190 |
| 2018/0055672 A1 * | 3/2018 | Erwin | A61F 5/0118 |

* cited by examiner

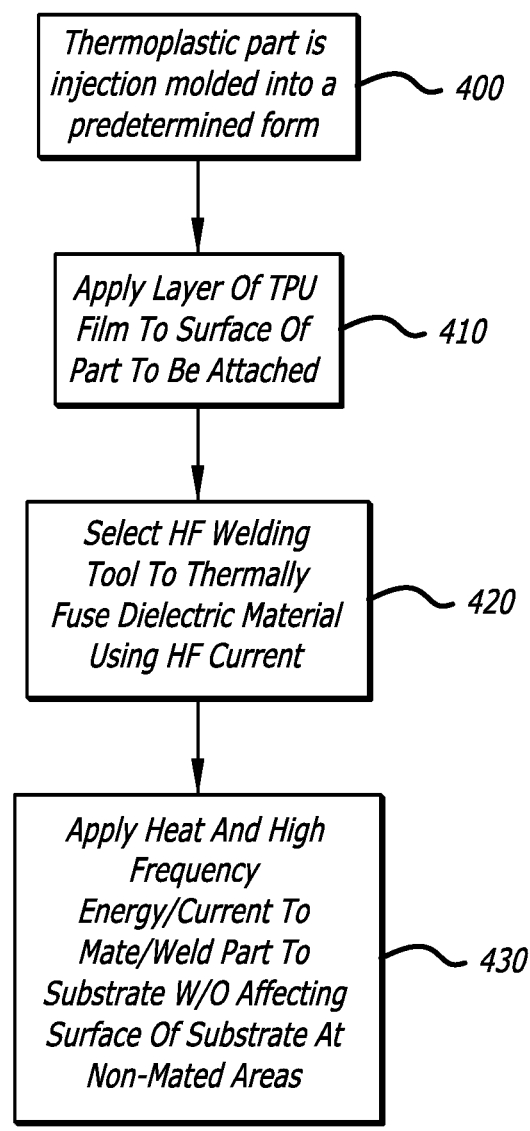

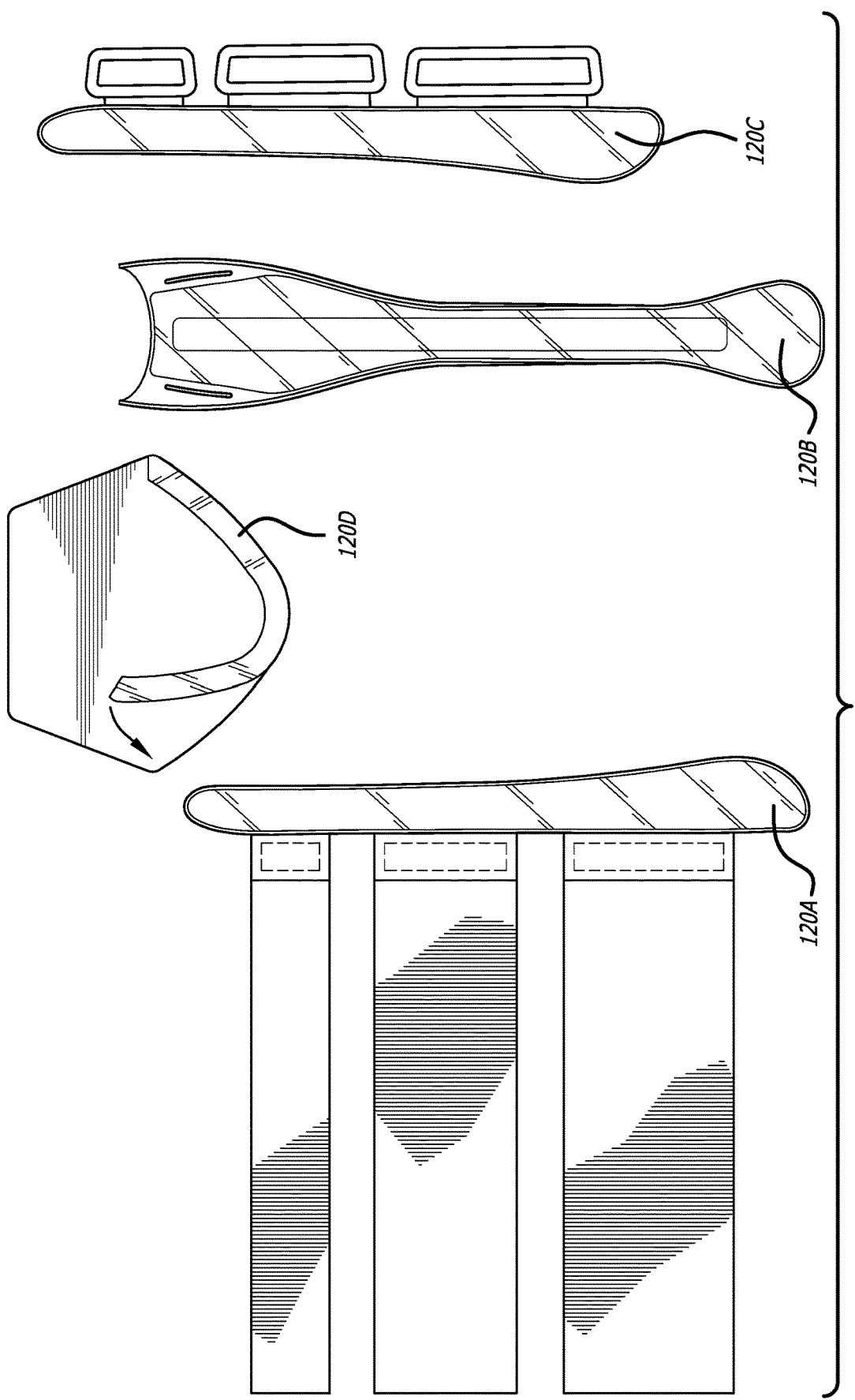

WRIST BRACE WITH WELDED THUMB SPICA AND METHOD FOR MAKING SAME

CROSS-REFERENCES TO RELATED APPLICATIONS

This application claims priority from U.S. Provisional Patent Application No. 62/717,706, filed Aug. 10, 2018, the content of which is incorporated herein by reference in its entirety.

BACKGROUND

Wrist, hand, and thumb orthoses have been in use for decades by physicians who need to immobilize their patients hand, wrist, fingers, and combinations thereof for various reasons including sprains, tendonitis, post-casted fractures, and post-surgical recovery. These semi-rigid braces, also referred to as upper extremity orthoses, are made from soft base materials such as open cell foam or felt laminate with added component materials sewn thereto. The added component can be used to strengthen the orthosis, and also to form pockets for retaining a reinforcing stay. The reinforcing stay that are inserted into the sewn-on components have typically been made of metal or a hard plastic and serve to increase the rigidity of the orthosis in certain regions of the brace. Fastening straps typically made of hook and loop material are also commonly sewn onto the base materials to fit the orthosis to the wearer's upper extremity. An example of such braces is U.S. Pat. No. 6,186,969 to Bell entitled "Wrist Brace."

While sewing the various components of the orthosis provides a secure attachment between two components and is much less sensitive to the compatibility of the mating materials, there are drawbacks to sewing as a mode of attachment. Sewing is time-consuming and labor intensive, and often requires specialized machinery that is expensive and prone to breakdowns. However, due to the nature of the materials (typically fabrics and open cell foam materials), sewing remains the only option for attaching both hard and soft materials to a base fabric. The present invention solves this problem and overcomes the shortcomings of the prior art.

SUMMARY OF THE INVENTION

An orthopedic brace is formed of a resilient or semi-resilient base material having an inner surface that interfaces with the anatomy of the wearer, and an outer surface opposite the inner surface and facing away from the anatomy. The base material embraces an anatomical body part and may comprise, for example, a resilient or rigid fabric that straps, snaps, zips, buckles, or otherwise attaches in a manner that secures the body part within the brace. On the outer surface of the base material, a support member such as a thermoplastic sheet, strip, or solid member is coupled/bonded/fused to the outer side of the resilient base material through a high frequency and/or heat welding technique. The attachment of the support member preferably ensures that the entire surface of the polymeric material in contact with the resilient base material is bonded (thermally fused/coupled) to the resilient base material without impairing or damaging the structure of the base material.

The reinforcement support member is strategically located to provide semi-rigid and/or rigid support to the anatomical body part for desired stability and control. The thermoplastic (polymeric) material is chosen by way of thickness, geometry, and durometer (hardness) to provide the desired rigidity and support required by the brace. Further, the thermoplastic (polymeric) material can be a continuous single piece bonded/coupled to the base material, or can be separated into multiple regions and bonded to the base material, where desired support is needed for added geometrical stability. The thermoplastic (polymeric) material bonded to the base material can be a homogenous thermoplastic material or a compound of different durometer thermoplastic material, or a compound of thermoplastic and malleable aluminum material. The judicious selection of the ratio of thermoplastic material and metal or other rigid material can provide the optimal thickness, strength, and flexibility of the support member for the selected application.

An important feature of the present invention is that, in some cases, the thermoplastic material bonded to the base material can be bonded to the base material over other components that are traditionally sewn to the base material, such as straps and d-rings, to secure/bond the straps and d-rings to the base material. That is, the attachment of the support member to the brace can also serve as a reinforcement to elements of the brace that have an inclination to fail or yield.

The present invention is characterized by a soft goods type upper extremity orthotic that utilizes a combination of heated 3D tooling, HF energy, and pressure to thermally bond injection molded elements to the outer layer of a base material used in orthopedic supports. The brace of the present invention may have multiple fused/welded/bonded/heat components that are strategically placed to offer support and restriction of movement of the wrist, hand, and/or thumb (WHT) for the treatment of injuries to the wrist, hand, and forearm. The components are secured to a base fabric without stitching and, in a preferred embodiment, without traditional adhesives, to provide a sturdy and robust wrist brace or upper extremity orthosis that can be manufactured far more efficiently than prior art wrist braces.

A first preferred embodiment of the present invention comprises a base laminate material having open cell urethane foam with fabric laminated to both an inner surface and the outer surface. Said base laminate could be of other material types including closed cell foams as well as felts or spacer fabrics. The base laminate material is pliable and flexible, and is designed to be worn against the skin without irritation or promoting sweating.

The base laminate material is reinforced on an outer surface with a thermoplastic composite sheet composed of a first thermoplastic layer and a laminated second thermoplastic film. The thermoplastic sheet is bonded onto the base laminate material by heat welding through high frequency energy, direct heat, or a combination thereof. When heat welding the thermoplastic sheet onto the base laminate material, a cavity is formed therebetween that is used as a pocket adapted to receive a metal or thermoplastic volar stay.

The attachment system of the present invention can be accomplished without sewing straps or fasteners onto the base laminate material, a feature not found in the prior art. This is accomplished by employing first and second thermoplastic injection molded elongate stays (support structures) that are bonded using heat welding to the outer surface of the base laminate foam. The injection molded elongate stays are associated with a respective ulnar side corresponding to the ulna bone and radial side corresponding to the radius bone, and provide support in the ulnar and radial regions of the brace where said thermoplastic injection molded stays are located. A thin film of thermoplastic polyurethane (TPU) film is used between the mating parts to facilitate the bonding operation and allow the rigid stays to be welded to the soft base laminate material.

In one preferred embodiment, the radial stay may be made of a thermoplastic polyurethane or other thermoplastic material and may further include multiple molded d-ring connectors at a peripheral edge that are joined via a thin bridge of thermoplastic material forming a pliable hinge. The pliable hinge allows for the flexion of the d-rings upward away from the radial stay, making it easy to slide the associated strap through the d-ring. The ulnar stay may be made of a thermoplastic polyurethane or other thermoplastic material and may further include three straps that are fastened to respective tabs extending from the ulnar stay. The three straps wrap around the wrist of the patient, are received by the respective d-rings, and then reattach on the ulnar side of the brace to provide a custom fit for the wrist brace.

In one preferred embodiment, a supplemental laminate material is attached to the base laminate material to form a lateral thumb outrigger. The thumb outrigger is U-shaped and narrows in the distal direction, and is adapted to allow the patient's thumb to exit the main portion of the wrist brace and be supported while restricting some movement of the thumb in all directions. The thumb outrigger can be fitted with a sleeve or elastic band to encompass and secure the thumb therein. The thumb outrigger is then bolstered by a thumb spica, a substantially rigid thermoplastic stay extending from the proximal end of the brace to the distal end of the thumb outrigger at the IP joint. The thumb spica can be reinforced with a metal spine molded into the spica to provide even greater rigidity to the brace and prevent the patient's thumb from extending in the direction of the thumb spica. The spica stay includes slots on the distal medial and/or lateral areas of the stay to receive a fastening member used to secure the stay circumferentially to the thumb. The proximal end of the spica stay is flared to reduce localized forces of the spica stay against the arm of the wearer.

The thumb spica in a preferred embodiment comprises an over molded radial gutter splint that is welded to the thumb outrigger using a TPU film. The thumb spica uses a softer over molded thermoplastic material over a more rigid reinforcing stay of, for example, aluminum. This construction allows the thermoplastic overmold to bend and conform comfortably around the thumb. A flared proximal end is formed to relieve localized forces at the end of the stay. In a preferred embodiment, the thumb spica has a pair of outwardly flared ears at a distal end, the flared ears opening outward in the distal direction corresponding loosely with a y-shaped configuration that can wrap around approximately 50% of the thumb. The ears include slits that receive a band dedicated to fastening the thumb to the thumb outrigger and the thumb spica, partially immobilizing the thumb.

The advantages and features of the present invention will best be understood with reference to the detailed description of the invention below along with the accompanying drawings listed here.

BRIEF DESCRIPTION OF THE DRAWINGS

FIG. 12 is a flow chart of the bonding operation of the present invention; and FIG. 13 illustrates the thermally activated sheets on the components to be bonded to the base layer.

DETAILED DESCRIPTION OF THE PREFERRED EMBODIMENTS

Figure 1:
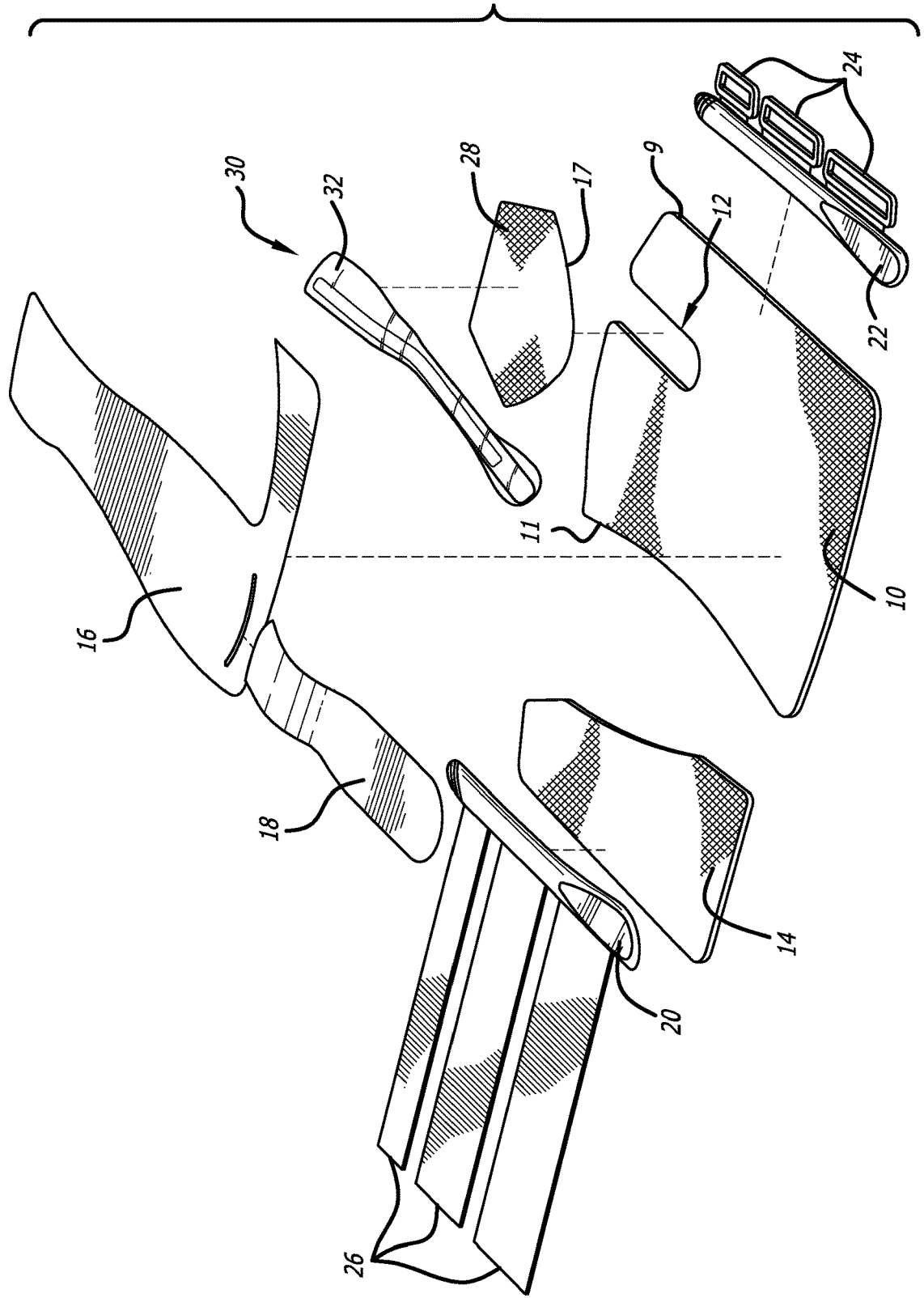
FIG. 1 is an exploded perspective view of the components of a first embodiment of the present invention.
Figure 2:
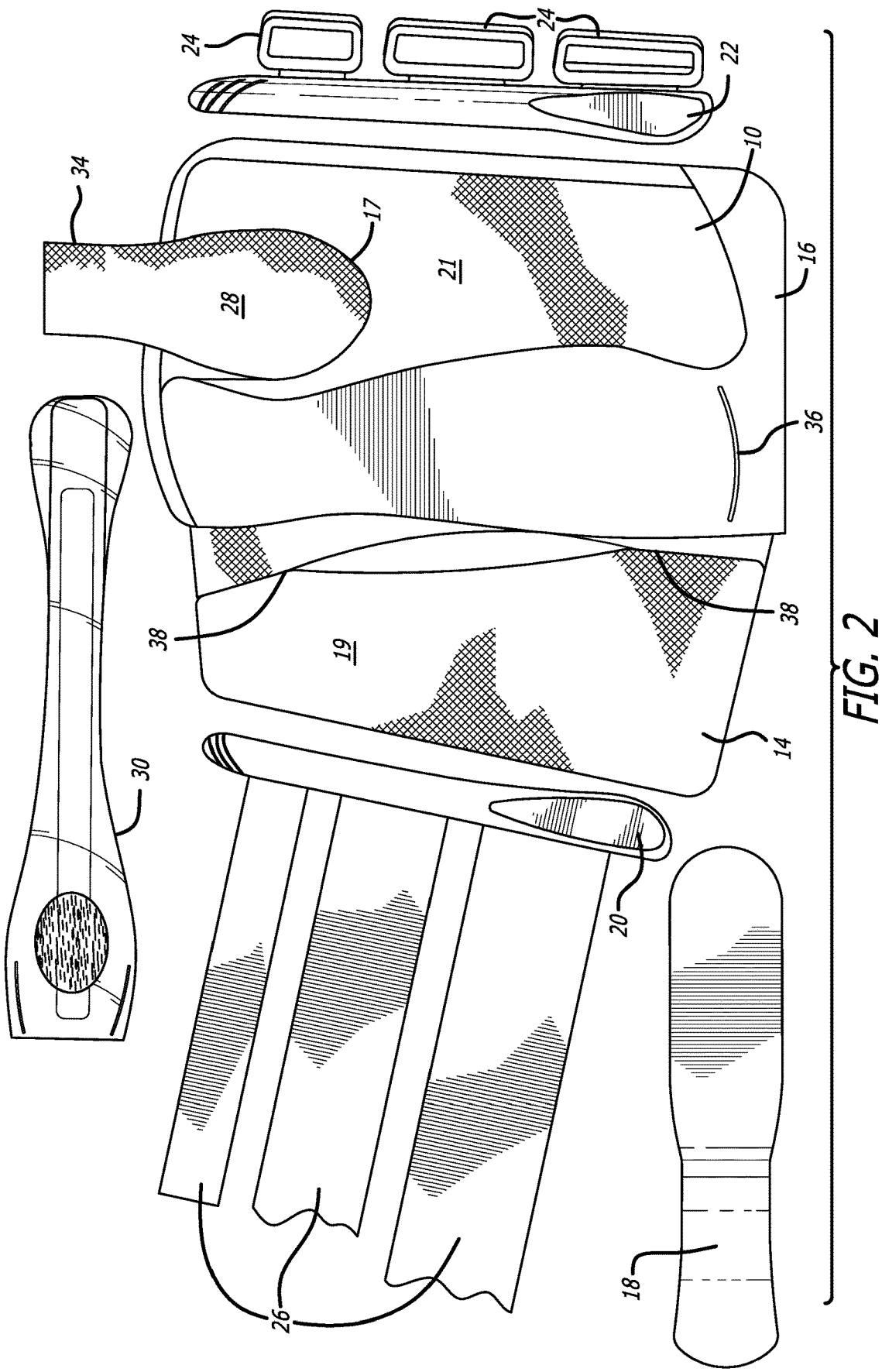
FIG. 2 is an elevated view of an arrangement of the components of the embodiment of FIG. 1.
Figure 3:
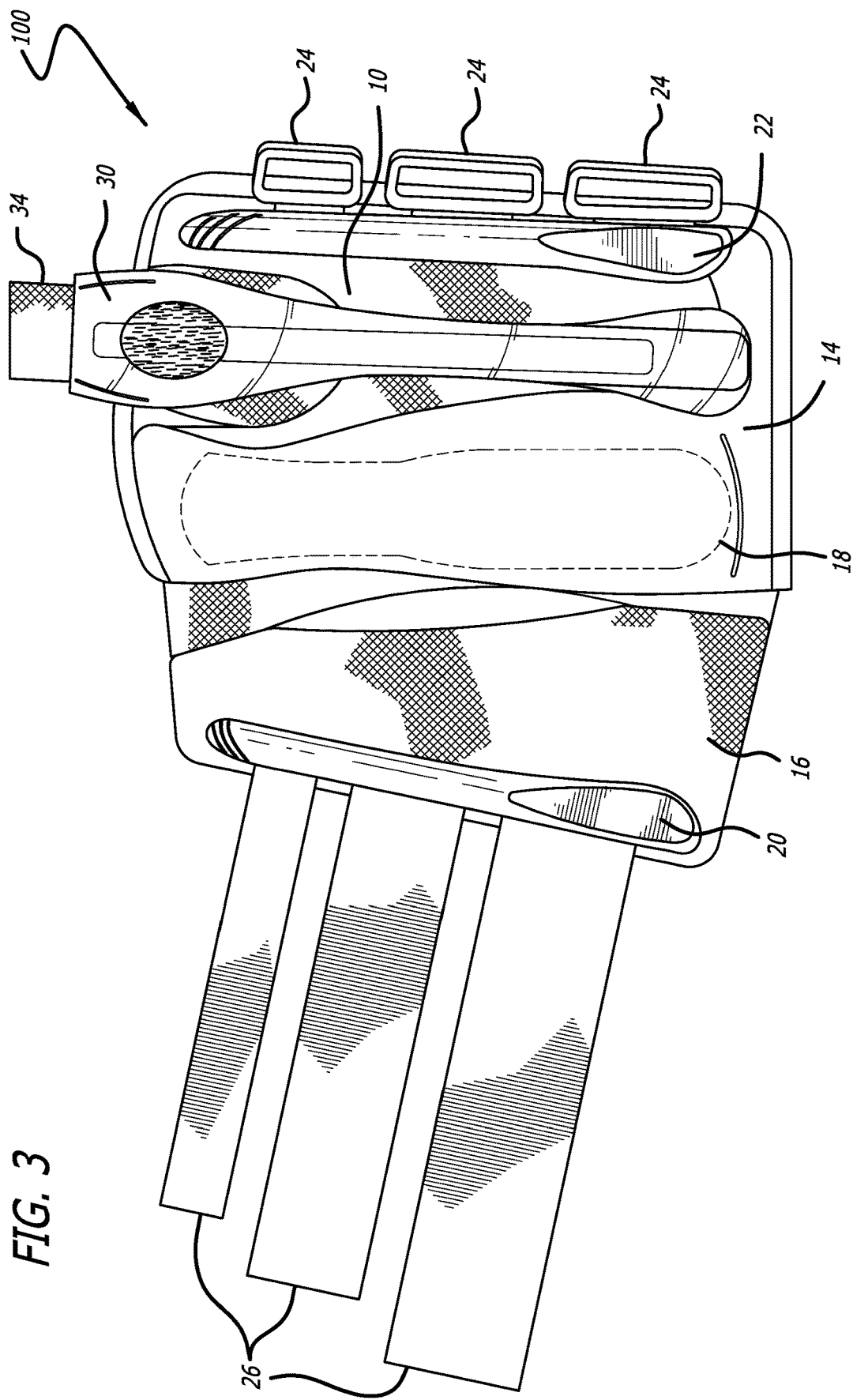
FIG. 3 is an elevated view of the assembled arrangement of the components of the embodiment of FIG. 1.

FIGS. 1-3 illustrate the components and general assembly steps for the constituents of a first preferred embodiment of a wrist brace embodying the aspects of the present invention. Base panel 10 comprises a base laminate material having a soft and flexible interior such as an open cell urethane foam that is sandwiched by outer layers of a laminated fabric material. The base laminate could also be of other material types including closed cell foams as well as felts or spacer fabrics. The resulting base panel 10 is a soft and flexible sheet that is adapted to comfortably wrap around the patient's hand, and preferably includes a U-shaped cut out 12 that will locate the attached thumb outrigger. The base panel 10 preferably provides a four way stretch to more comfortably fit the patient's hand, but such stretch is limited in order to securely fit the patient's hand. The base laminate has a continuous peripheral edge that may be separated into a radial side 9 that runs along the radius side of the brace and an ulnar side 11 that run along the ulnar side.

A thermoplastic composite panel 16 is applied over the base laminate panel 10 to add reinforcement to the brace 100. Thermoplastic composite panel 16 is preferably constructed of a first thermoplastic layer and a laminated second thermoplastic film, wherein the film is heat activated to facilitate a thermal bond via direct heat, high frequency, or a combination thereof to the base laminate panel 10. An extension panel 14 is preferably made of more elastic, stretchable material similar to the material as the base panel; 10 and is attached at the ulnar side 11 of the base laminate panel 10. When the thermoplastic composite panel 16 is peripherally bonded to the base panel 10 in a heat welding operation, a gap or pocket 36 is formed therebetween that is sized to receive a metal or thermoplastic volar stay 18.

Figure 9:
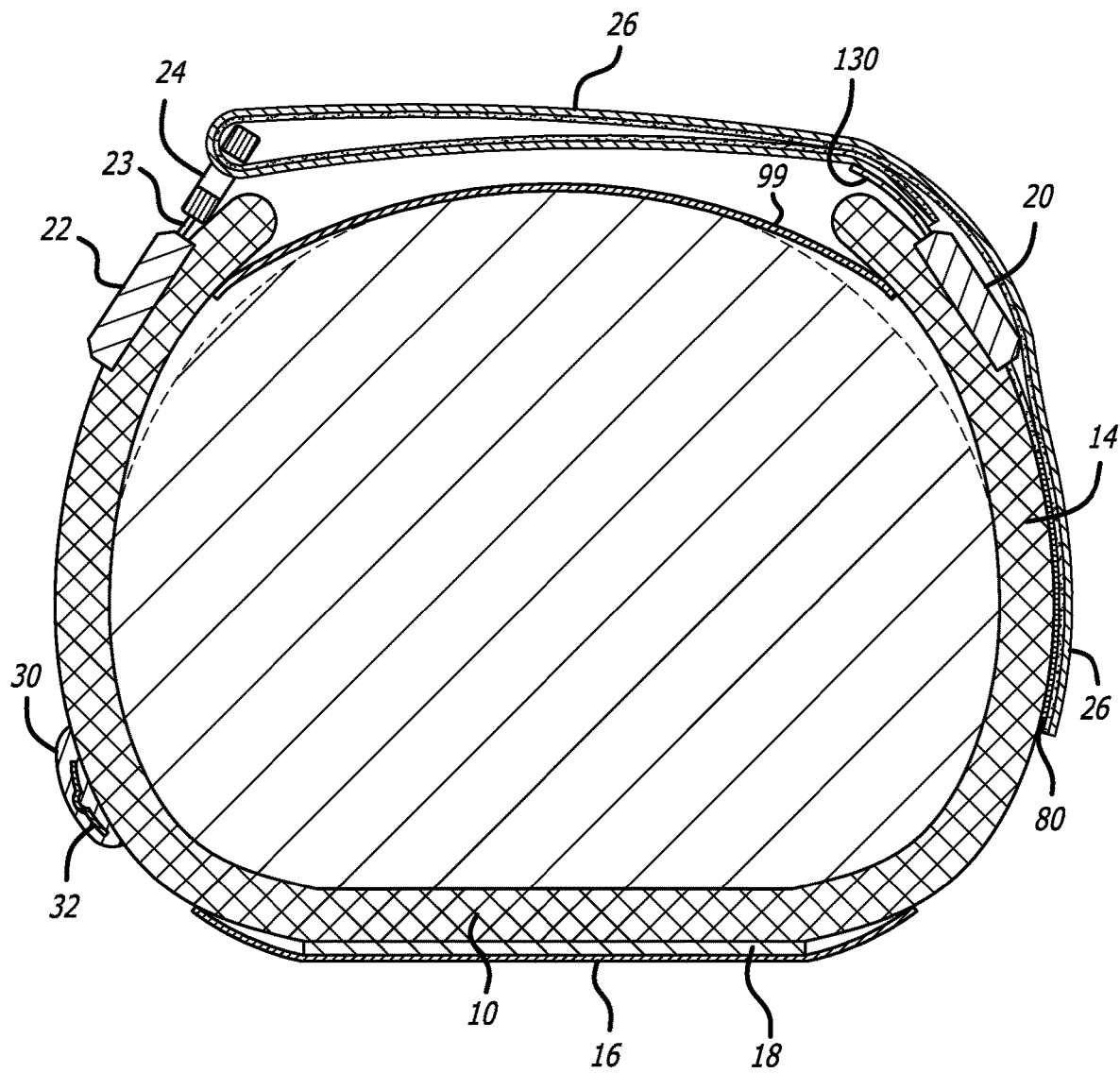
FIG. 9 is a cross-sectional view taken along lines 9-9 of FIG. 7.

The brace preferably further comprises a pair of thermoplastic injection molded outer stays 20,22 that have a stiffness that is greater than base laminate material but less than the volar stay 18. The thermoplastic injection molded outer stays 20, 22 are bonded directly to the outer surface of the base laminate panel 10 and the extension panel 14 via activation of a thin TPU film 120A, C (see FIG. 13) as more fully described below. The radial outer stay 22 may be made of a thermoplastic polyurethane or other thermoplastic material and may further include multiple molded d-rings 24 at a peripheral edge that are attached via a thin bridge of thermoplastic material forming a pliable hinge 23 (see FIG. 9). The pliable hinge 23 allows for a flexion and rotation of the d-rings away from the limb, making it easier to slide the corresponding connecting straps 26 through the d-ring 24. The straps 26 are sewn, glued, welded, or otherwise attached to the ulnar outer stay 20, and each strap includes hook and loop fastener material for attaching the strap either to itself or to the extension panel 14 after passing through its corresponding d-ring 24.

Figure 4:
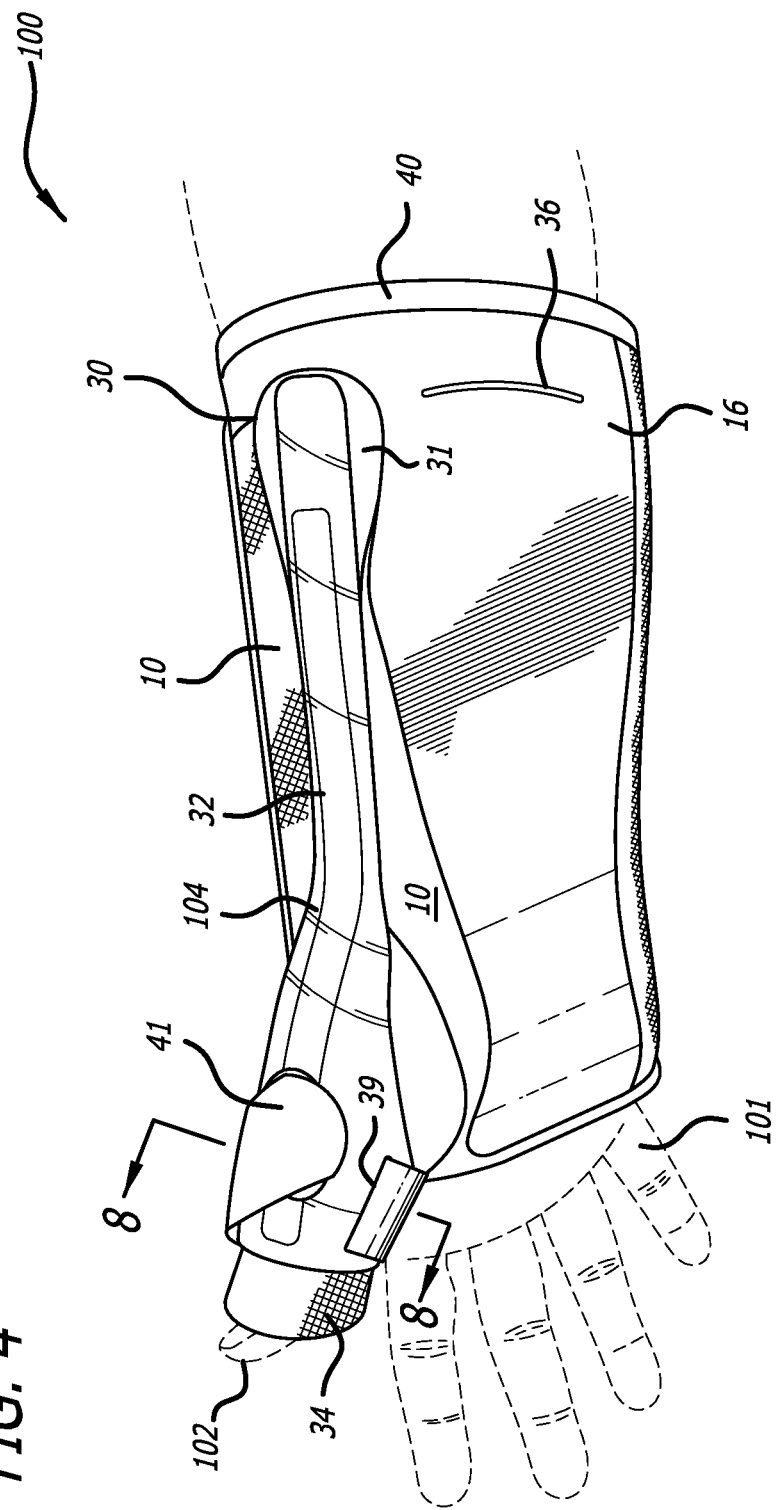
FIG. 4 is a radial side perspective view of the embodiment of FIG. 1.

A supplemental laminate panel 28 may be thermally bonded to the peripheral edge of base panel 10 at the U-shaped gap 12 using a thermoplastic urethane (TPU) film material 120D (see FIG. 13) to form a thumb outrigger 34. A substantially rigid thumb spica 30 in the form of an elongate thermoplastic element molded about an aluminum stay 32, is subsequently thermally bonded with a thin TPU film 120B to the base panel 10 and additionally bonded to the thumb outrigger 34 to establish a support for the thumb. With the thumb spica in place and attached as shown in FIG. 4, the extension of the thumb away from the fingers is effectively eliminated while some movement in the opposite direction (toward the fingers) is permitted by the brace. This feature has the benefit of protecting the thumb tendons while allowing the patient some grasping function needed to perform some basic tasks.

FIG. 2 illustrates a first stage of construction of the brace 100 of the present invention. The supplemental laminate panel 28 is bonded along edge 17 to the base panel 10 at the U-shaped gap 12 to form the thumb support outrigger 34. The thumb support outrigger 34 is generally semi-cylindrical and cradles the thumb as it narrows in the distal direction to match the width of the thumb it supports. The soft foam material may be selected so that the thumb outrigger does not chaff or irritate the skin even after long periods of wear. In a preferred embodiment, the attachment of the supplemental laminate panel 28 to the base panel 10 is achieved without stitching or adhesive, but rather the bonding occurs through an application of high frequency energy in combination with a thin TPU thin film 120D that allows the thumb outrigger 34 to attach directly to the foam laminate of the base panel 10. This feature is not found in the prior art.

FIG. 2 further illustrates the bonding of the thermoplastic composite panel 16 directly onto the base panel 10. This bonding takes place without stitching and, in a first preferred embodiment, without adhesive. A slit 36 in the thermoplastic composite panel 16 provides the insertion point for the aluminum volar stay 18 into the pocket or gap between the base panel 10 and the thermoplastic composite panel 16. The fabric extension panel 14 is attached along a first seam 38 to the ulnar side 11 of the base panel 10 to establish an expansion zone 19 of the brace that has greater stretch when compared with the thermoplastic reinforced area 21 of the base laminate material 10. Stated another way, the non-reinforced extension panel 14 is capable of greater stretch than the base panel 10 reinforced with the thermoplastic composite panel 16, so greater yield occurs on the ulnar side of the brace 100 where comfort is usually more important than rigidity. Conversely, the radial side of the brace is more rigid to more tightly secure the thumb and the associated ligatures.

FIG. 3 illustrates the assembled brace 100. The ulnar outer stay 20 and the three straps 26 are bonded/welded to the opposite edge of the extension panel 14 using a TPU film 120A (see FIG. 13) on the thermoplastic stay, where the straps can be sewn, bonded, or otherwise attached to tabs 130 (see FIG. 9) extending from the outer stay 20. The radial outer stay 22 and the d-rings 24 are bonded to the base panel 10 using a TPU film 120C on the outer stay 22. The ability to bond the stiffer outer stays 20, 22 directly onto the flexible fabric of the extension panel 14 and the base panel 10, respectively, without stitching or adhesives, is not found anywhere in the prior art and represents a major advance in the manufacturing process. Other prior art braces have attempted to use injection molding to integrate a component into a material, but injection molding requires dies and other expensive equipment not required by the present invention. Moreover, the components of brace 100 can all be bonded simultaneously or in multiple steps, as opposed to sewing a first element and then sewing a second element, and so on until all elements are attached.

FIG. 3 further illustrates the thumb spica 30 that is bonded directly to both the base laminate panel 10 and the thumb outrigger 34 using TPU film 120B. The present invention's direct welding technique allows the rigid thermoplastic thumb spica 30 to be directly welded onto the fabric surface of the base panel 10 without adhesive or stitching, and simultaneously welded onto the fabric thumb outrigger 34. No other prior art brace achieves this consolidation of a rigid support member onto a soft fabric covering in the manner described herein.

FIGS. 4-7 illustrate the fabricated brace 100 of the present invention fitted onto a patient's hand 101. FIG. 4 illustrates the brace 100 from below, where the thermoplastic composite panel 16 covering the base laminate panel 10 is prominently shown. The slit 36 in the composite panel 16 allows ingress and egress of the aluminum volar stay 18 into the pocket or gap formed between the thermoplastic composite panel 16 and the base panel 10. FIG. 4 illustrates an outer peripheral binding 40 that may be added around the perimeter of the brace 100 to limit stretching at the perimeter while allowing some expansion at the interior, especially the expansion zone 19 at the extension panel 14. The thumb spica 30 (see also FIGS. 10A, B) is shown having a generally flat proximal end 31 with a rounded, widened contact area that better distributes any torque or transferred forces resulting from movement of the thumb 102 and propagated down the spica.

Figure 8:
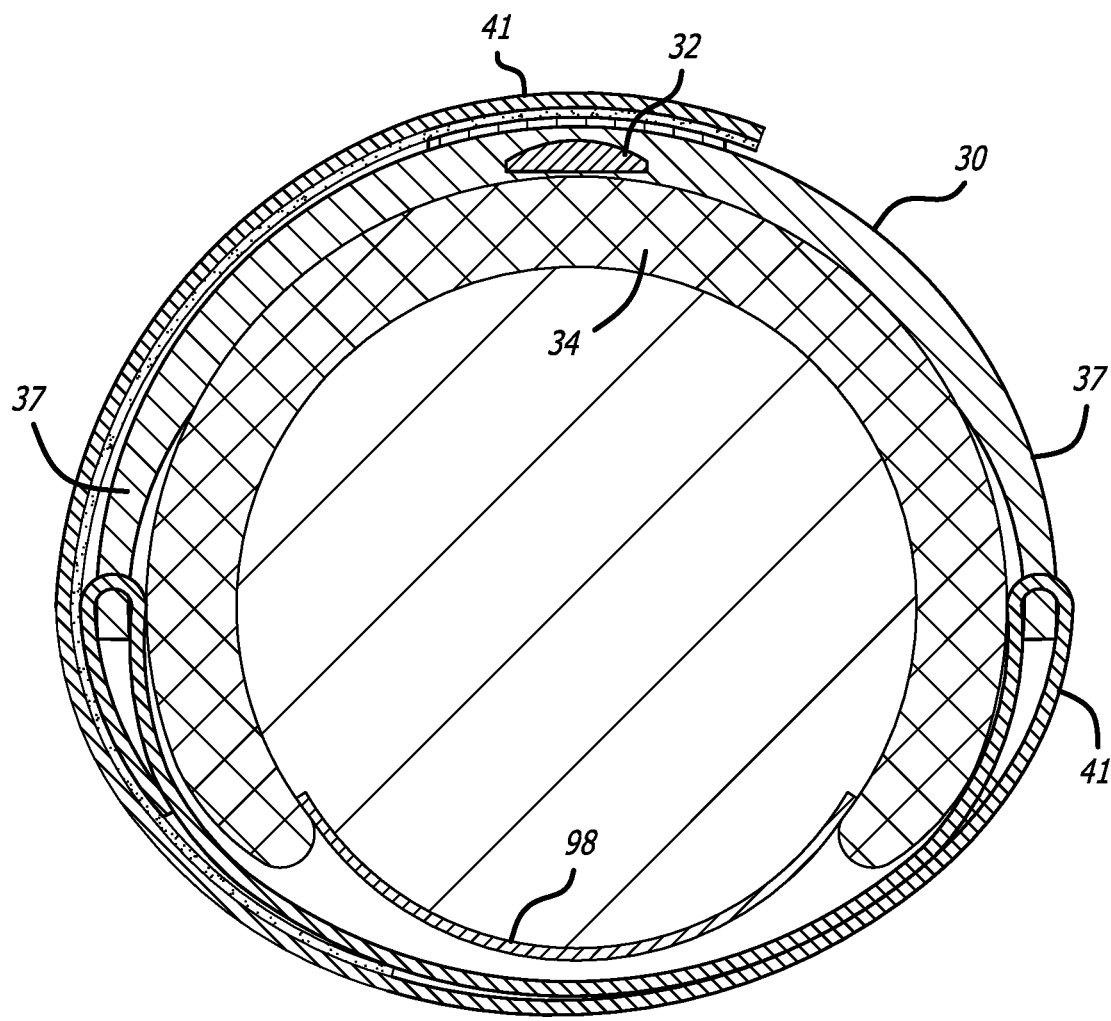
FIG. 8 is a cross-sectional view taken along lines 8-8 of FIG. 4.
Figure 10A:
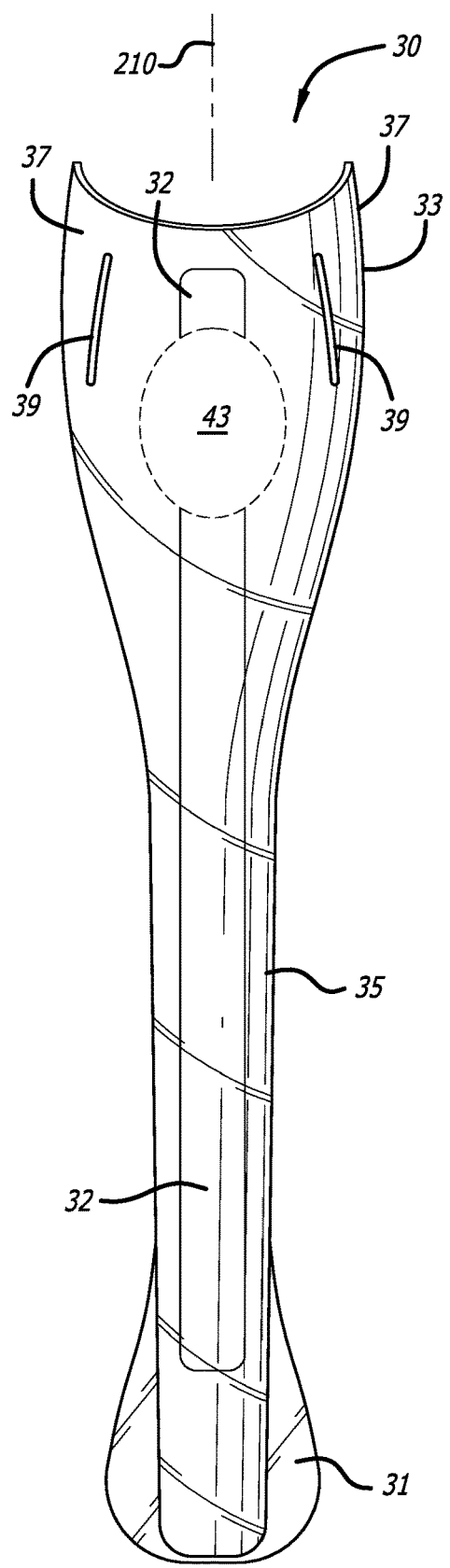
FIGS. 10A and 10B are front and side views, respectively, of the thumb spica of the embodiment of FIG. 1.
Figure 10B:
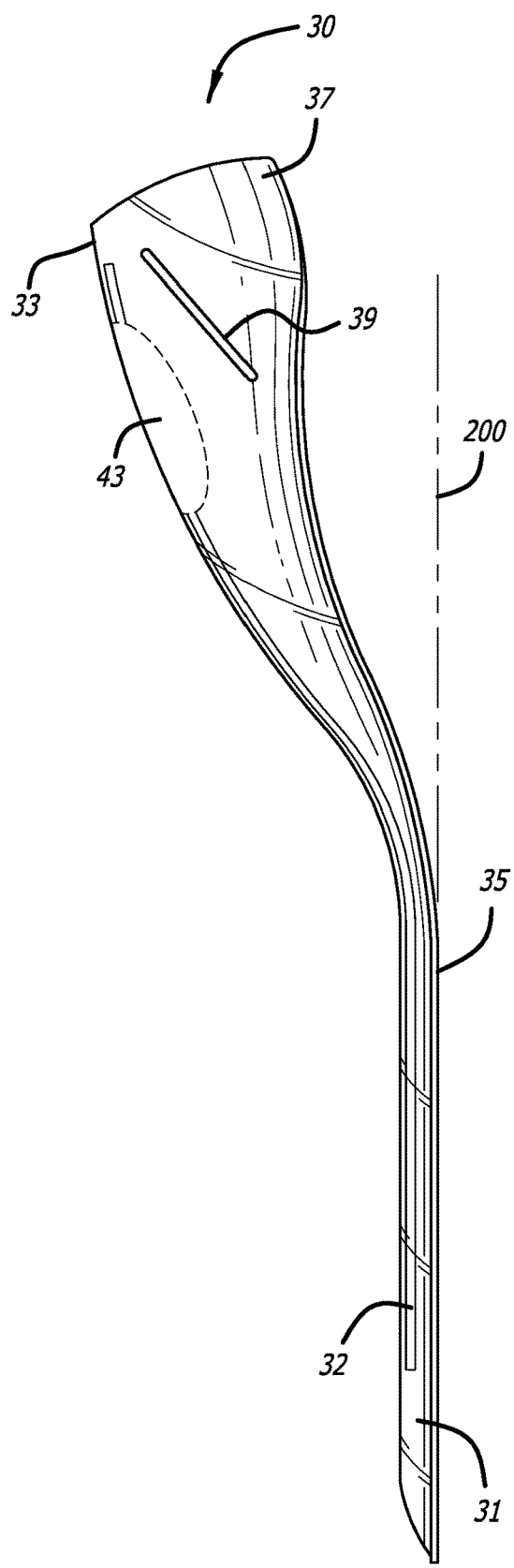

The thumb spica 30 is preferably overmolded and may be transparent or translucent to reveal an aluminum inner support stay 32 permanently disposed inside the thumb spica 30, where the appearance of the inner support stay 32 through the transparent thermoplastic may give a patient and/or physician added security and confidence in the function of the thumb spica 30. The middle portion 35 of the thumb spica 30 remains substantially narrow and in plane 200, and then transitions at the base 104 of the thumb so as to be angled out of plane 200 and widening at the distal end 33. The distal end 33 of the spica 30 can be formed with rounded ears 37 (best seen in FIGS. 10A, B) that cooperate to form a more parabolic (rather than circular) profile, opening radially outward to provide some additional lateral movement of the thumb between the two ears 37. As shown in FIGS. 10A, B, the distal end 33 of the thumb spica 30 is curved about a longitudinal axis 210 and away from, and offset from, the plane 200 in which the proximal end lies. FIG. 8 illustrates the thumb support portion of the wrist brace in cross section taken along lines 8-8 of FIG. 4, including a tubular webbing 98 that can be sewn into the thumb support to better position the thumb inside the thumb support.

The thumb spica 30 may be formed with a diagonal slit 39 in each ear 37 that receives a band 41 (see also FIG. 5) that wraps around the thumb 102 and retains the thumb in the parabolic cradle of the curved distal end. The band 41 maybe attached by sewing or other means to a first ear 37 and then wraps around the thumb and passes through the opposite slit and back to the original ear until the thumb is completely circumnavigated. A patch 43 of hook material can be used as an anchor where the end of the band 41, having a complimentary area of loop material, fastens the band 41 in place after securing the thumb.

Figure 5:
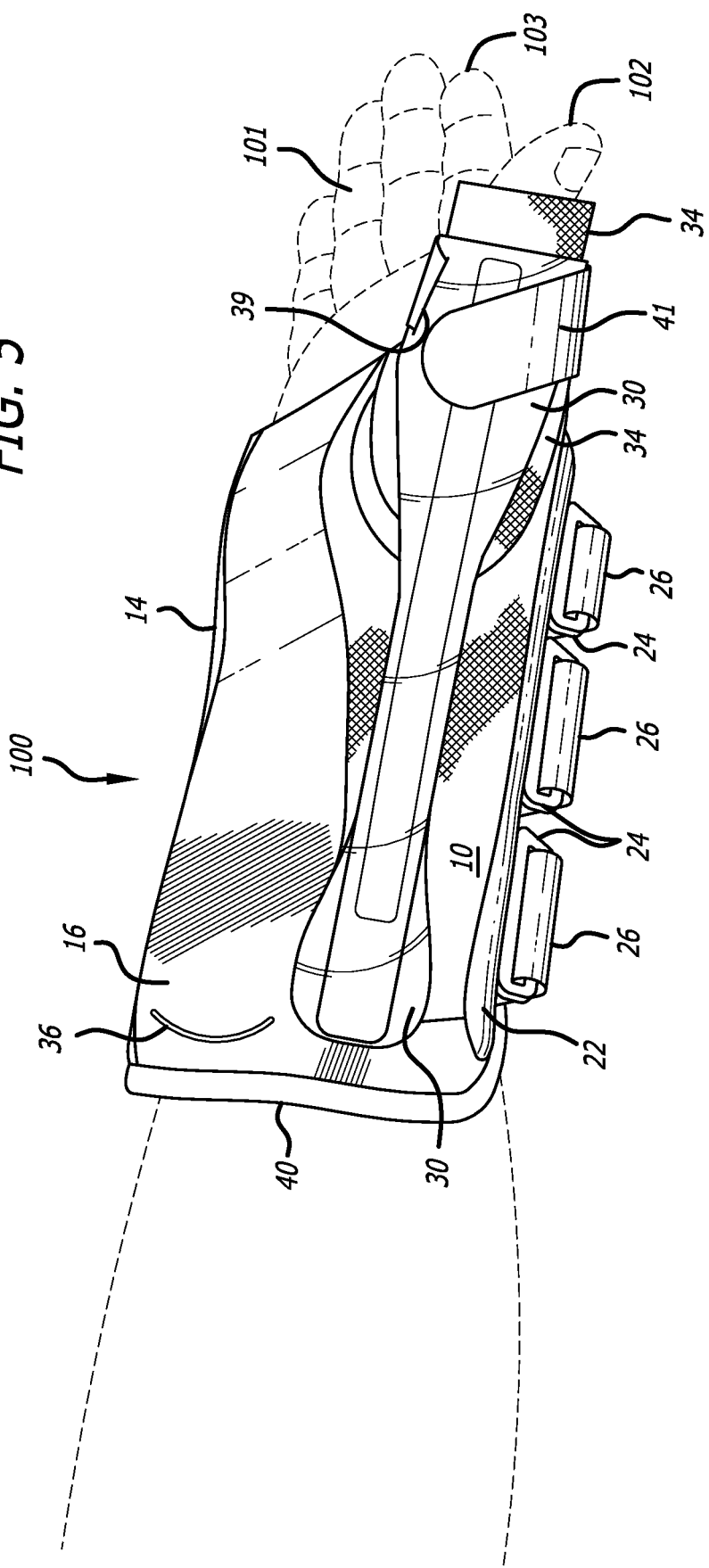
FIG. 5 is another radial side perspective view of the embodiment of FIG. 1.

FIG. 5 illustrates another view of the brace 100 on a patient's hand. The thumb spica 30 partially encircles the patient's thumb and the band 41 wraps and secures the thumb inside the spica 30 between the ears 37. The thumb outrigger 34 extends just beyond the distal end of the thumb spica 30 to cushion the thumb 102 while the spica 30 limits flexure of the thumb away from the index finger 103. Slit 36 in the thermoplastic composite panel 16 allows a temporary and transitional stay to be inserted and removed from the brace 100, whereas thumb spica 30 is rigidly and permanently attached to the brace.

Figure 6:
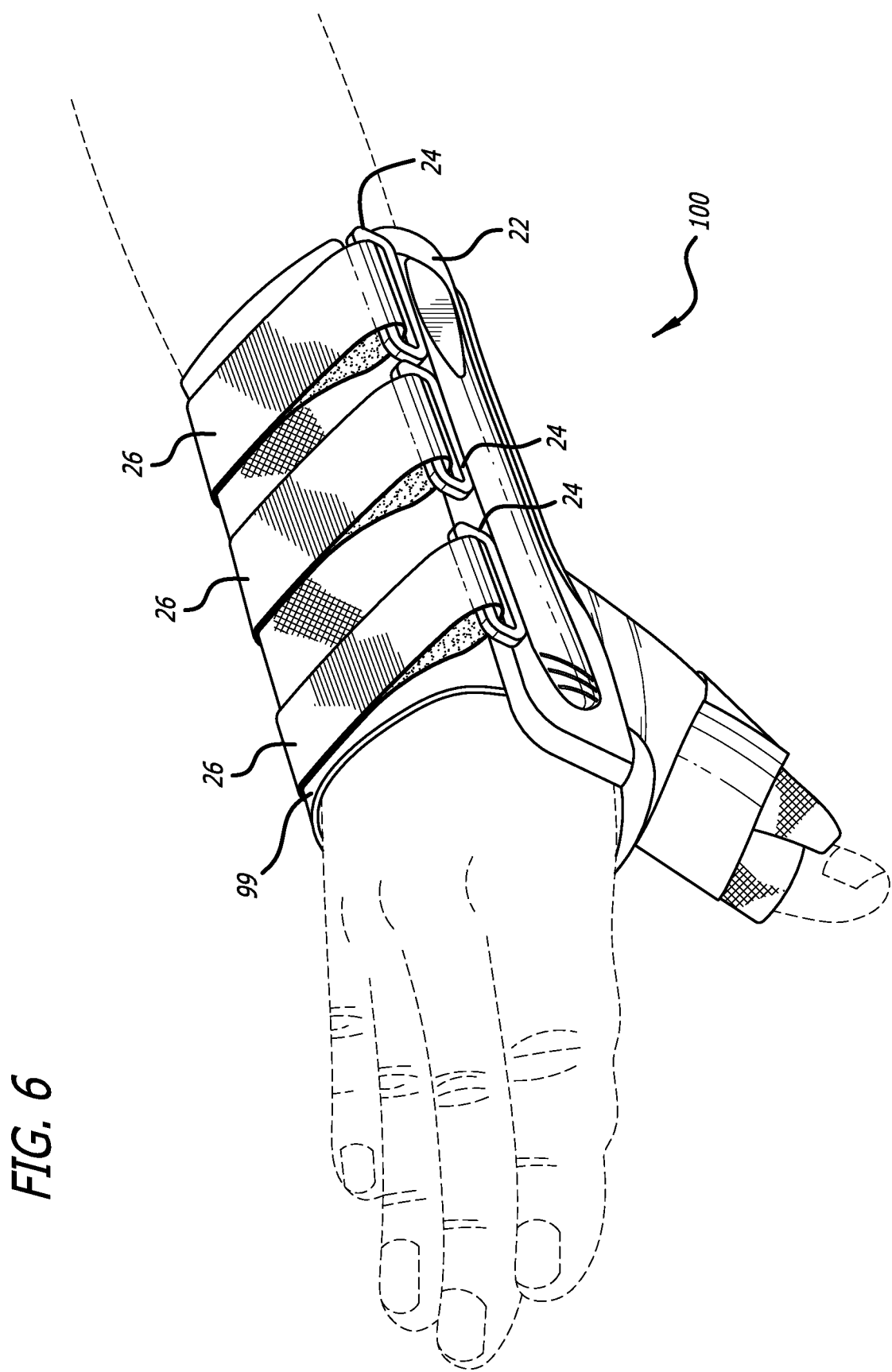
FIG. 6 is a perspective view of an underside of the embodiment of FIG. 1.
Figure 7:
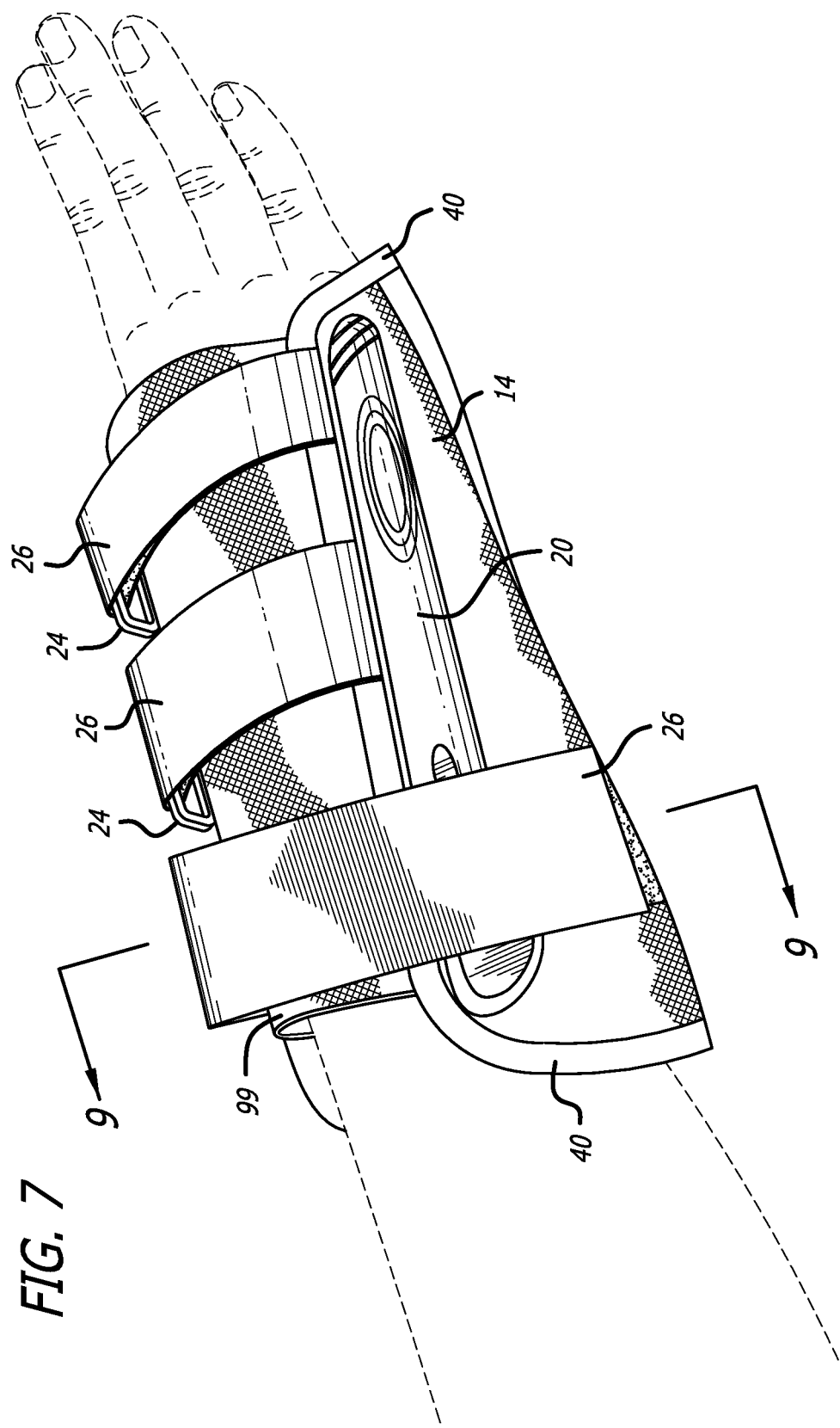
FIG. 7 is an elevated, perspective side view of the embodiment of FIG. 1.
Figure 11:
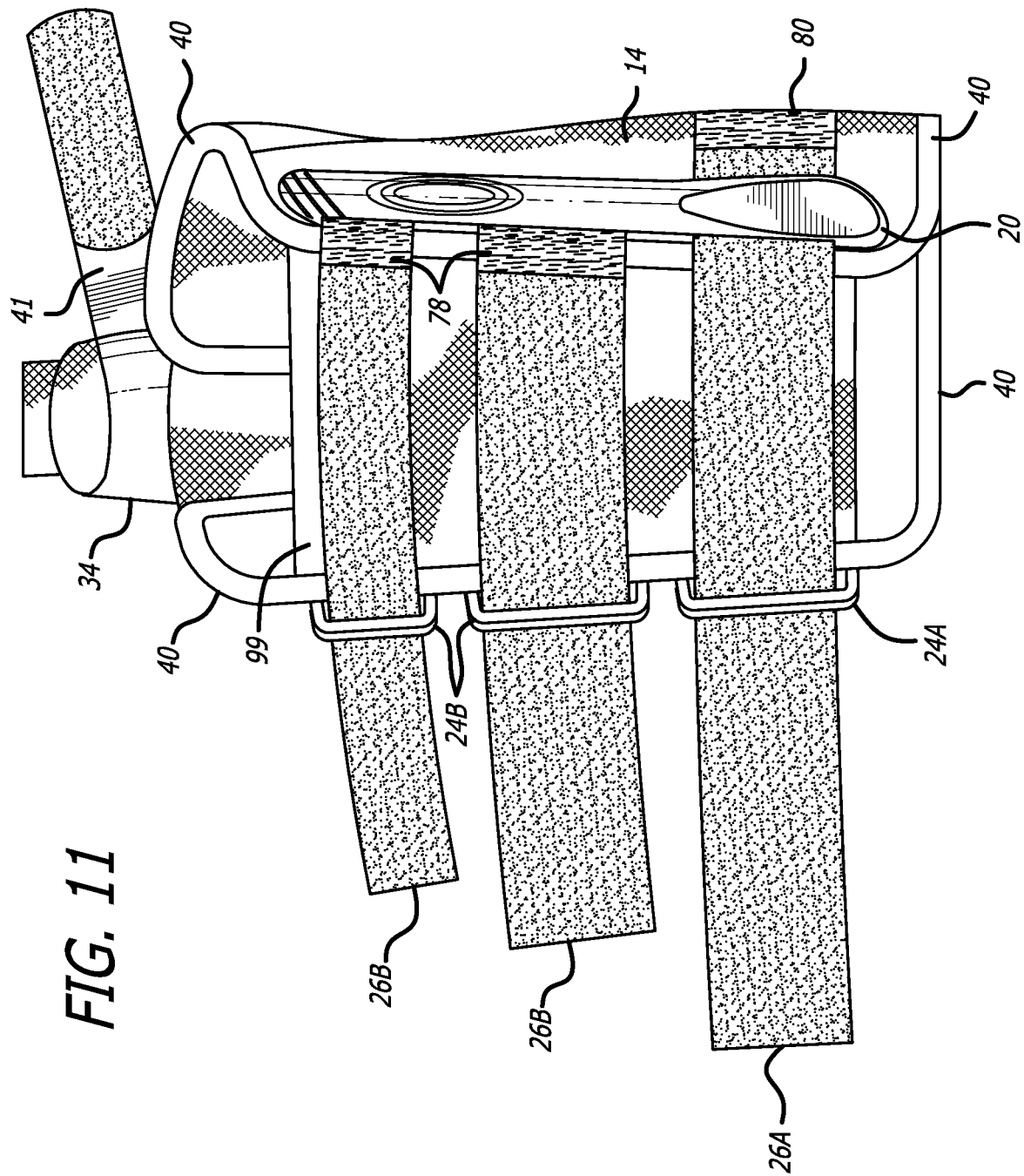
FIG. 11 illustrates an underside view of the embodiment of FIG. 1.

FIGS. 6 and 7 illustrate how the brace 100 is secured to the patient's wrist using the straps 26 and d-rings 24. The radial outer stay 22 is welded onto the base panel 10 using TPU film 120C and the stay includes three d-rings 24 attached by a flexible or pliable hinge 23 that allows the d-rings 24 to rotate or flex away from the stay 22 to facilitate threading the straps 26 through. The ulnar outer stay 20 is welded onto the extension panel 14 using TPU film 120A and anchors the three straps 26 on the ulnar side. The three straps 26 are passed through their corresponding d-rings 24 and back onto themselves where hook and loop material are used to attach and secure the fit of the straps 26. FIG. 11 illustrates the preferred attachment points for the three straps 26. For the proximal strap 26A, the strap passes through the proximal d-ring 24A and extends over itself and over the ulnar outer stay 20 where it attaches to a hook and loop material anchor 80 on the extension panel 14. The two distal straps 26B both pass through their respective d-rings 24B and attach prior to the ulnar outer stay 20 at hook and loop material anchors 78 on the reverse side of the straps 26B. In a preferred embodiment, a soft fabric sleeve 99 is sewn into the interior of the brace 100 to further cushion the user's hand and add comfort to the brace 100.

The methodology for bonding the outer stays, the thumb spica, and the supplemental panel to the outer fabric of the base composite panel 10 and/or the outer fabric of the extension panel 14 will now be discussed with respect to the present invention. Prior methods for fusing/welding/bonding/adhering an injection molded plastic component to a base fabric substrate without adhesive is absent in the art. Rather, prior art braces required that the base material be placed in the injection mold, and a molten thermoplastic resin would be added under extremely high pressure to the mold to infiltrate the material and harden about and within the material. Of course, placing the material inside the heated injection molding and subjecting the material to high temperatures and high pressures irreversibly degrades the soft pliable material and resulted in a weaker and more abrasive fabric. Other attempts sought to glue or stitch the components together, with inferior results. Specifically, liquid adhesives used on fabric surfaces are prone to failure and can otherwise damage or disfigure the non-mating surfaces, and stitching can weaken the material and lead to tearing and separation. Stitching also results in raised surfaces at the threading that can rub or irritate the skin. In the present invention, the stays, spica, and thumb outrigger are bonded to the base panel 10 and the extension panel 14 using either heat or high frequency energy to achieve a bond. The benefits of the present invention include preserving the characteristics of the base fabrics, ease of manufacture, expediency, cost savings, and flexibility to weld a variety of materials that heretofore could not be easily combined.

FIG. 12 illustrates a sequence for constructing the brace 100 using the novel techniques of the present invention. Initially, a thermoplastic part such as the outer radial stay 22 is injection molded into a predetermined form (preferable material is TPU) in step 400. Once the part is formed, a bonding layer of heat activated film 120C, such as TPU film 120C, is heat staked to the joining surface of the molded plastic piece in step 410. A pre-heated, high-frequency welding tool that is preferably the same shape as the injection molded plastic form (either a one sided or double sided tool) is then selected in step 420 to activate/energize the TPU film and thermally fuse/weld/bond/adhere the thermoplastic part to the outer surface of the base composite material 10. The energy applied to the bonding step can be HF (high/radio frequency) electrical current, heat, or a combination thereof, to complete the bonding operation of step 430. If subsequent bonding operations are necessary, the process is repeated for each attachment or the bonding operations can be conducted in parallel by using multiple tools simultaneously.

Settings for heat welding a part to its mating substrate vary depending upon the volume, density and thickness of the part and substrate. A combination of heat and HF power is preferably applied during the welding process to allow the TPU film to bond the mating part to the substrate without adverse effects to the substrate, maintaining the form and function of the substrate, and without affecting the surface finish of the injection molded part. Softgood components can be bonded to each other using the TPU film as well, such as the thumb outrigger 34 (a foam material) that is bonded to the base panel 10 (another fabric/foam composite) prior to the thumb spica 30 being welded to the base 10 and thumb outrigger 34.

Current welding parameters for three exemplary products utilizing the present invention are as follows:

| Sample | Power kW | Heat Temp (C.) | Pressure (psi) | Weld Time (s) | Heat Time (s) |
| --- | --- | --- | --- | --- | --- |
| Ankle Brace | 9 | up mold 250° down mold 90° | 40 | 32 | 20 |
| Back Brace | 9 | up mold 270° down mold 60° | 30 | 20 | 10 |
| Wrist Brace | 6 | 130° | 60 | 15 | 10 |

The temperature ranges for heat welding in the present invention is in the range of 75° C.-200° C., and the power ranges from 2 kW to 30 kW. The pressure applied in the bonding process can vary from 10 psi-200 psi, and the heat activated film (TPU) may have a thickness between 0.1 mm and 0.8 mm. The injection molded thermoplastic (TPU-thermoplastic urethane) hardness of the stays and the thumb spica range of 30 shore A to 90 shore D. Note in a preferred embodiment, a cooling step is performed after the weld to set the weld. A cooling metal bar, plate, or other chilled device can be pressed against the film after heating to accelerate the cooling process, where the temperature of the materials is lowered below melting, to ambient temperature, or below ambient prior to the application of the high frequency energy.

Another feature of the present invention is the capacity of the thermoplastic film welding technique to bond curved stays to the base material. This three dimensional "contouring" is not present with the prior art injection molding. In addition, the thermoplastic films used to bond the supporting materials to the fabric base can be selected to be waterproof and form a barrier to moisture, whereas adhesives tend to be broken down by water and eventually fail.

Although specific embodiments have been described and depicted in the foregoing description and drawings, the invention is not limited to these embodiments and the invention is properly interpreted to cover many orthoses that would benefit from the inventions and concepts disclosed herein. Nothing in this disclosure should be construed as limiting or excluding other embodiments unless expressly stated. Further, the scope of the invention is properly measured by the words of the appended claims, using their customary and ordinary meanings in light of, but not confined by, the foregoing descriptions and depictions.

We claim:

1. An upper extremity orthotic comprising:
a flexible, stretchable fabric base panel configured to at least partially wrap around a patient's wrist;
a thermoplastic reinforcing panel overlaid onto the base panel;
a thumb outrigger comprised of a flexible, stretchable fabric and having a thermoplastic film on a first edge, the thumb outrigger welded onto the base panel at the first edge; and
a rigid thermoplastic thumb spica extending from a proximal edge of the base panel to a distal end of the thumb outrigger, the thumb spica having a thermoplastic film on a first side, the thumb spica welded to the base panel and the thumb outrigger at the first side.

2. The upper extremity orthotic of claim 1, further comprising an injection molded outer radial stay and an injection molded outer ulnar stay, each including a thermoplastic film on a first surface, each welded onto the base panel at said respective first surfaces, whereby the radial and ulnar stays include fastening elements to fit the orthotic to the patient's wrist.

3. The upper extremity orthotic of claim 2, wherein the base panel comprises a reinforced composite member and a non-reinforced extension member.

4. The upper extremity orthotic of claim 3, wherein the radial outer stay is welded to the reinforced composite member and the ulnar outer stay is welded to the non-reinforced extension member.

5. The upper extremity orthotic of claim 4, further comprising an anchor patch for releasably attaching the band to an outer surface of the thumb spica.

6. The upper extremity orthotic of claim 2, wherein each thermoplastic film is activated by direct heat to bond to a surface of the base material.

7. The upper extremity orthotic of claim 6, wherein each thermoplastic film is also activated by high frequency energy to bond to a surface of the base material.

8. The upper extremity orthotic of claim 2, wherein a pocket is formed between the base panel and the thermoplastic reinforcing panel, said pocket sized to receive a volar stay therein.

9. The upper extremity orthotic of claim 8, further comprising a volar stay.

10. The upper extremity orthotic of claim 2, wherein the base panel includes a U-shaped cut out, and wherein the thumb outrigger is attached to the base panel about the U-shaped cut out.

11. The upper extremity orthotic of claim 2, wherein each thermoplastic film is activated by high frequency energy to bond to a surface of the base material.

12. The upper extremity orthotic of claim 2, further comprising a pliable hinge connecting a first of the outer radial stay and the outer ulnar stay with a respective fastening element.

13. The upper extremity orthotic of claim 1, further comprising a band passing through slots at a distal end of the thumb spica to secure a patient's thumb to the outrigger.

14. The upper extremity orthotic of claim 13, where the thumb spica includes outwardly flared first and second ears at a distal end, the band passing through each outwardly flared ear.

15. The upper extremity orthotic of claim 14, wherein the outrigger further comprises a tubular webbing between the outwardly flared ears of the thumb spica.

16. The upper extremity orthotic of claim 14, wherein the outwardly flared ears of the thumb spica are adapted to cradle a patient's thumb and resist lateral movement of the thumb.

17. The upper extremity orthotic of claim 1, wherein the thumb spica is reinforced with an internal, permanent metal stay.

18. The upper extremity orthotic of claim 17, wherein the thumb spica is made of a light transmitting material to reveal the internal, permanent metal stay.

19. The upper extremity orthotic of claim 1, wherein an ulnar region includes an expansion zone having a greater elasticity than a radial area that is reinforced with the thermoplastic reinforcing panel.

20. The upper extremity orthotic of claim 1, wherein the thumb spica includes a proximal section that is lies in a first plane, a middle section that curves out of the first plane, and a distal section that is curvilinear about a longitudinal axis and offset from the first plane.

21. The upper extremity orthotic of claim 1, further comprising a fabric sleeve attached to the base panel for receiving a patient's wrist therein.

22. The upper extremity orthotic of claim 1, further comprising an outer binding on the periphery of the base panel to limit an elasticity of the base panel at the periphery.

23. A method for manufacturing an orthotic, comprising: providing a base panel formed of a stretchable, porous fabric; selecting a plurality of injection molded thermoplastic reinforcing members; applying a thin, thermoplastic polyurethane film (TPU) to a first surface of the reinforcing members; placing the reinforcing members onto the base panel; and applying high frequency energy to the interface between the reinforcing members and the base panel at the thermoplastic polyurethane film (TPU) to bond the reinforcing member to an exterior surface of the base panel without subjecting the base panel or the reinforcing member to the high frequency energy outside of the interface.

24. The method for manufacturing an orthotic of claim 23, further comprising the step of applying direct heat to the interface without subjecting the base panel or the reinforcing member to direct heat outside of the interface.

25. The method for manufacturing an orthotic of claim 24, further comprising a step of cooling the interface to below ambient temperature after the applying of direct heat and prior to the applying of high frequency energy.

26. The method for manufacturing an orthotic of claim 23, wherein the orthotic is a wrist brace.

27. The method for manufacturing an orthotic of claim 23, further comprising the step of applying at least ten (10) psi of pressure to the thermoplastic polyurethane film (TPU).

28. The method for manufacturing an orthotic of claim 23, wherein the reinforcing members have a Shore hardness of greater than 30 Shore A.

29. The method for manufacturing an orthotic of claim 23, wherein an application of high frequency energy sufficient to bond the reinforcing members to the base panel takes less than sixty (60) seconds.

30. The method for manufacturing an orthotic of claim 23, wherein an application of high frequency energy occurs within a range of six to nine kilowatts.

31. The method for manufacturing an orthotic of claim 23, wherein the thermoplastic polyurethane film (TPU) has a thickness in the range of between 0.1 mm and 0.8 mm.

32. A thumb spica for an upper extremity orthotic, comprising a proximal section, and middle section, and a distal section, wherein:
   the proximal section is substantially planar with a rounded periphery and a width of the proximal section reduces in the distal direction;
   the middle section includes a constant width portion and an expanding width portion, the expanding width portion distally transitioning out of plane with the proximal section; and
   the distal section comprising an arc about a longitudinal axis that increases in the distal direction and terminating in first and second flared ears; and
   a metal stay extending interiorly from the proximal section to the distal section.

33. The thumb spica of claim 32, wherein the first and second flared ears each include a slit adapted to receive a band therethrough.

34. The thumb spica of claim 33, further comprising a band sized to pass through the slit of the first and second flared ears and adapted to attach to an outer surface of the thumb spica.

35. The thumb spica of claim 32, wherein the thumb spica is made of a light transmitting material and the metal stay is visible through the light transmitting material.

36. The thumb spica of claim 35, wherein the light transmitting material is a thermoplastic injection molded component.

* * * * *